(12) United States Patent
Yang et al.

(10) Patent No.: US 9,310,636 B2
(45) Date of Patent: Apr. 12, 2016

(54) LIQUID CRYSTAL CELL, LIQUID CRYSTAL DISPLAY DEVICE AND SURFACE MODIFICATION METHOD FOR INFRARED MATERIAL

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Jiuxia Yang, Beijing (CN); Feng Bai, Beijing (CN); Yiming Zhao, Beijing (CN); Xiao Sun, Beijing (CN); Bing Bai, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 82 days.

(21) Appl. No.: 14/348,773

(22) PCT Filed: Aug. 28, 2013

(86) PCT No.: PCT/CN2013/082473
§ 371 (c)(1),
(2) Date: Mar. 31, 2014

(87) PCT Pub. No.: WO2014/176847
PCT Pub. Date: Nov. 6, 2014

(65) Prior Publication Data
US 2015/0103293 A1    Apr. 16, 2015

(30) Foreign Application Priority Data
Apr. 28, 2013    (CN) .......................... 2013 1 0157493

(51) Int. Cl.
*G02F 1/133*     (2006.01)
*G02F 1/1333*   (2006.01)
(Continued)

(52) U.S. Cl.
CPC .......... *G02F 1/133382* (2013.01); *C09K 11/08* (2013.01); *G02F 1/1335* (2013.01);
(Continued)

(58) Field of Classification Search
CPC .................... G02F 1/133382; G02F 1/133514; G02F 1/133512; G02F 1/133528; G02F 1/132; G02F 1/133365; G02F 1/1334; G02F 1/133377; G02F 1/133345; C09K 11/08; C09K 19/38; C09K 19/60
USPC .......................................... 349/20, 21, 22, 84
See application file for complete search history.

(56) References Cited

U.S. PATENT DOCUMENTS 6,133,979 A * 10/2000 Komatsu ........... G02F 1/133382
349/161

FOREIGN PATENT DOCUMENTS

CN         1642375 A  *  7/2005  ................ G02F 1/13
CN       20070069399 A    7/2007

OTHER PUBLICATIONS

International Search Report for International Application No. PCT/CN2013/082473 issued Jan. 27, 2014, 9pgs.
(Continued)

*Primary Examiner* — Mike Qi
(74) *Attorney, Agent, or Firm* — Ladas & Parry LLP

(57) ABSTRACT

A LCD device comprising the liquid crystal cell and a surface modification method for an IR material are provided. The IR material is obtained via the surface modification method, and a component comprising the IR material is disposed in the liquid crystal cell. As the liquid crystal cell can emit infrared light, it is beneficial for healthy. The surface modified IR material is compatible and has optimal matching property with the structure of the liquid crystal cell, the heat exchange capacity between the IR material and the backlight as well the ambient light can be improved without compromising the performance of the LCD device, and the surface modified IR material will emit far-IR light of specific wavelength with higher emissivity.

11 Claims, 1 Drawing Sheet

(51) Int. Cl.
*G02F 1/1335* (2006.01)
*C09K 11/08* (2006.01)
*A61N 5/06* (2006.01)

(52) U.S. Cl.
CPC .... *G02F1/133512* (2013.01); *G02F 1/133514* (2013.01); *G02F 1/133528* (2013.01); *A61N 2005/066* (2013.01); *A61N 2005/0659* (2013.01); *G02F 2203/11* (2013.01)

(56) References Cited

OTHER PUBLICATIONS

International Preliminary Report on Patentability Appln. No. PCT/CN2013/082473; Dated Nov. 3, 2015.

* cited by examiner

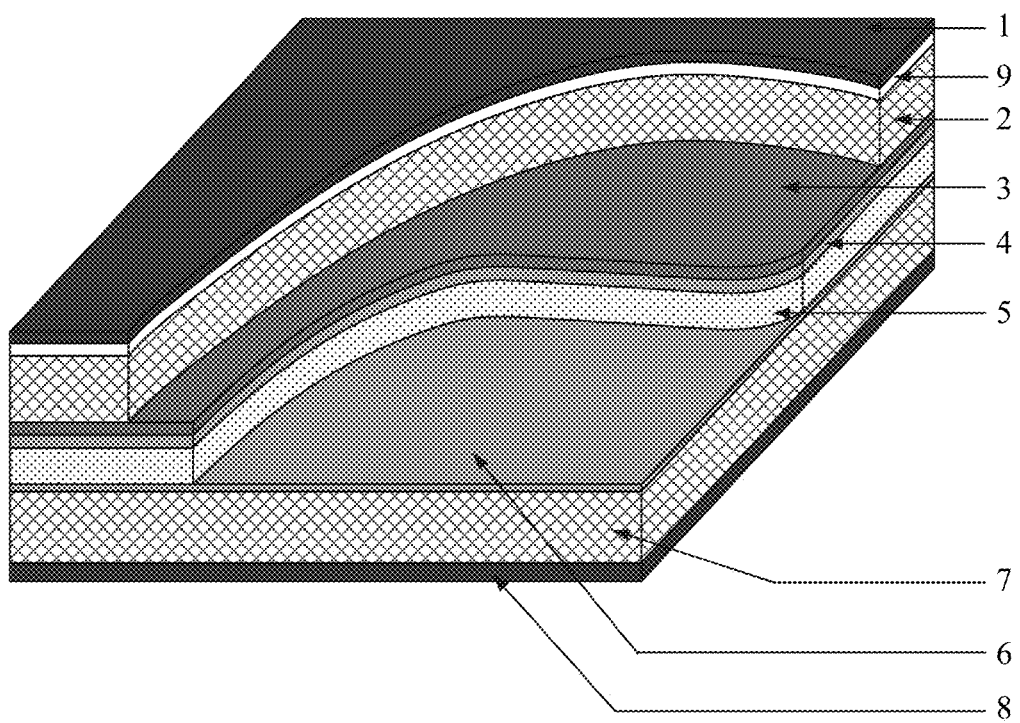

LIQUID CRYSTAL CELL, LIQUID CRYSTAL DISPLAY DEVICE AND SURFACE MODIFICATION METHOD FOR INFRARED MATERIAL

CROSS REFERENCE TO RELATED APPLICATIONS

This application is based on International Application No. PCT/CN2013/082473 filed on Aug. 28, 2013, which claims priority to Chinese National Application No. 201310157493.5 filed on Apr. 28, 2013. The entire contents of each and every foregoing application are incorporated herein by reference.

FIELD OF THE ART

Embodiments of the invention relate to the field of liquid crystal technologies, more particularly, to a liquid crystal cell, a liquid Crystal Display (LCD) device, a surface modification method for an Infrared (IR) material, and a liquid crystal cell provided with a component comprising an IR material obtained via the surface modification method.

BACKGROUND

With the rapid development of display technologies, people expect display devices to provide display effect with high definition, high contrast ratio and high brightness; moreover, there are more diverse requirements on the functions of the display devices, such as entertaining and healthy functions.

SUMMARY

Embodiments of the invention provide a liquid crystal cell, a LCD device, a surface modification method for an IR material and a liquid crystal cell provided with a component comprising the IR material obtained via the surface modification method, so as to emit IR light when irradiated by light.

A first aspect of the invention provides a liquid crystal cell, wherein a component comprising an infrared (IR) material is disposed in the liquid crystal cell.

As an example, the component comprising the IR material is an IR layer made of the IR material.

As an example, the liquid crystal cell comprises a color filter substrate and an array substrate disposed as opposed to each other, the IR layer is disposed on the color filter substrate and/or the array substrate.

As an example, the IR layer is disposed on all or a part of a surface of the color filter substrate.

As an example, the color filter substrate is divided into a pixel region and a black matrix region surrounding the pixel region, the IR layer is formed on one of the pixel region and the black matrix region.

As an example, the liquid crystal cell further comprises a upper polarizer disposed at one side of the color filter substrate and a common electrode disposed at the other side of the color filter substrate; the color filter substrate comprises a substrate and a color filter layer, wherein the IR layer is disposed between the upper polarizer and the substrate; or the IR layer is disposed between the substrate and the color filter layer; or the IR layer is disposed between the color filter layer and the common electrode.

As an example, the liquid crystal cell further comprises a lower polarizer, the array substrate comprises a substrate and a pixel electrode;

wherein the IR layer is disposed between the pixel electrode and the substrate; or the IR layer is disposed between the lower polarizer and the substrate.

As an example, the component comprising the IR material comprises at least one of the following components: an upper polarizer, an upper substrate, a color filter layer, a common electrode, a pixel electrode, a lower substrate and a lower polarizer.

As an example, the liquid crystal cell comprises an upper polarizer, an upper substrate, a color filter layer, a common electrode, a pixel electrode, a lower substrate and a lower polarizer, at least one of which is made of a material comprising the IR material.

As an example, the IR material is a mixture of one or more of biochar, tourmaline, far-infrared ceramic, jade powder, aluminum oxide, copper(II) oxide, silver(I,III) oxide and silicon carbide.

As an example, a particle size of the IR material is in the order of a nanometer to a micrometer.

As an example, the IR material is surface modified so as to emit IR light upon being irradiated.

A second aspect of the invention provides a LCD device comprising a backlight module and any of the above liquid crystal cells.

A third aspect of the invention provides a surface modification method for an IR material, comprising:

nanocrystallizing the IR material to obtain nanoparticles of the IR material; and modifying surface property of the nanocrystallized nanoparticles such that the nanoparticles are compatible and have matching property with a corresponding structural layer of a liquid crystal cell and emit IR light when being irradiated by light.

As an example, nanocrystallizing the IR material comprises grinding and dispersing the IR material to obtain a dispersion solution of the IR material with an average particle size of 1 nm to 200 nm.

As an example, modifying surface property of the nanocrystallized nanoparticles comprises:

mixing the dispersion solution of the IR material with an organic solvent containing methyl methacrylate, styrene, maleimide and then adding an azo-initiator solution into the mixture; and upon finishing the reaction, adding a cooling organic solvent to cool and stirring until a resultant is cooled, then filtering and drying the resultant to obtain the surface modified IR material.

As an example, a molar ratio between methyl methacrylate, styrene and maleimide is 1:1~2:1~2, the IR material weights 8~25% of the total mixture weight; and the azo-initiator solution is added drop by drop with a weight of 1~5% of total monomer weight.

As an example, an environmental condition for modifying the surface property of the nanocrystallized nanoparticles has a temperature of 35° C.~60° C. and is in a nitrogen atmosphere;

a reaction time is 30 minutes to 90 minutes;

a temperature of the cooling organic solvent is 5° C. to 10° C.;

cooling is performed till room temperature;

filtering is performed for three times; and drying is performed for 5 minutes to 20 minutes at 70° C. to 100° C.

A fourth aspect of the invention provides a liquid crystal cell, wherein a component comprising an IR material is disposed in the liquid crystal cell, the IR material is obtained using the above surface modification method.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

FIG. 1 schematically illustrates a configuration of a liquid crystal cell in accordance with an embodiment of the invention.

NUMERAL REFERENCES

1—upper polarizer; 2—upper substrate; 3—color filter layer; 4—common electrode; 5—liquid crystal; 6—pixel electrode; 7—lower substrate; 8—lower polarizer; 9—IR layer.

DETAILED DESCRIPTION

In order to make objects, technical details and advantages of the embodiments of the invention apparent, the technical solutions of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

In addition to "an array substrate", "a color filter substrate" and "liquid crystal filled between the array substrate and the color filter substrate" as appreciated by a person of ordinary skill in the art, the term "liquid crystal cell" further comprises "a upper polarizer" overlaying at one side of the color filter substrate opposite to the liquid crystal and "a lower polarizer" overlaying at one side of the array substrate opposite to the liquid crystal.

An embodiment of the invention provides a liquid crystal cell, in which a component comprising an IR material is disposed. For example, the component comprising the IR material may be an IR layer made of the IR material. It will be described in detail with reference to FIG. 1.

FIG. 1 illustrates a liquid crystal cell in accordance with an example of the invention, which comprises an upper polarizer 1, an upper substrate 2, a color filter layer 3, a common electrode 4, liquid crystal 5, a pixel electrode 6, a lower substrate 7, a lower polarizer 8 and an IR layer 9. Generally, the upper substrate 2 and the color filter layer 3 form a color filter substrate, whereas the lower substrate 7 and the pixel electrode 6 form an array substrate. The upper and lower substrates 2 and 7 may be made of a transparent material such as glass to facilitate the transmission of light. Therefore, the liquid crystal cell comprises the color filter substrate and the array substrate disposed as opposed to each other. In the embodiment, the IR layer 9 is disposed on the color filter substrate, i.e., between the upper substrate 2 and the upper polarizer 1. It can be appreciated that the IR layer 9 may also be disposed on the array substrate, or disposed on both the color filter substrate and the array substrate.

It can be contemplated that individual components of the liquid crystal cell in practical applications may be different from that illustrated in FIG. 1, which is for illustrative purpose only.

The IR layer 9 comprises a material that generates IR light via heat exchange (abbreviated as IR material). The IR material may absorb energy when being irradiated, so as to emit IR light with a wavelength typically of 0.77 μm~1 mm. Moreover, the intensity of the IR light may be controlled through particle size, surface morphology and content of the available ingredient of the IR material.

The above IR material may be a mixture of one or more of biochar, tourmaline ($[Na,K,Ca][Mg,F,Mn,Li,Al]_3[Al,Cr,Fe,V]_6[BO_3]_3[Si_6O_{18}][OH,F]_4$), far-infrared (far-IR) ceramic, jade powder, aluminum oxide, copper(II) oxide, silver(I,III) oxide and silicon carbide. The particle size of the IR material may be for example in the order of a nanometer to a micrometer.

As illustrated in FIG. 1, the IR layer 9 is disposed between the upper polarizer 1 and the upper substrate 2. The disposition may be realized by using the following method:

cleansing the upper substrate 2;

coating the IR layer 9 on a back surface (that is, a surface of the upper substrate 2 that faces the upper polarizer as illustrated) of the upper substrate 2 and curing the IR layer 9; and forming the color filter layer 3 on a front surface of the upper substrate 2.

As an example, forming the color filter layer 3 on a front surface of the upper substrate 2 comprises:

forming a black matrix on the front surface of the upper substrate 2;

forming Red, Green and Blue (R\G\B) sub-pixels; and forming a spacer.

In the above method, a protection layer may be further coated on the IR layer 9 after coating the IR layer 9. A function of the protection layer is to prevent the IR layer 9 from being damaged during the fabrication of the color filter layer 3. After fabricating the color filter layer 3, the protection layer on the IR layer 9 may be peeled off.

Alternatively, other than disposing the IR layer 9 between the upper polarizer 9 and the upper substrate 2 as illustrated in FIG. 1, the IR layer 9 may also be disposed between the upper substrate 2 and color filter layer 3. The disposition may be realized by using the following method:

cleansing the upper substrate 2;

coating the IR layer 9 on a front surface (that is, a surface of the upper substrate 2 that is opposite to the upper polarizer 1) of the upper substrate 2 and curing the IR layer 9;

forming the color filter layer 3 on the IR layer 9.

As an example, forming the color filter layer 3 on the IR layer 9 comprises:

forming a black matrix on the IR layer 9;

forming R\G\B sub-pixels; and forming a spacer.

Whether the IR layer 9 is disposed between the upper polarizer 1 and the upper substrate 2 or between the upper substrate 2 and the color filter layer 3, the IR layer 9 can be considered as being disposed on the color filter substrate. In this case, the IR layer 9 may be coated on the entire surface of the color filter substrate or on a part of the surface of the color filter substrate. For example, the IR layer 9 may be coated on region having the black matrix, or region having the R\G\B sub-pixels, of the color filter substrate, such that the corresponding region can emit IR light or the intensity of the IR light in the corresponding region can be enhanced.

It is noted that the IR layer 9 may also be disposed on other locations of the liquid crystal cell in other examples of the invention. For example, the IR layer 9 may be disposed between the color filter layer 3 and the common electrode 4, or between the pixel electrode 6 and the lower substrate 7, or between the lower substrate 7 and the lower polarizer 8, and the like.

Another embodiment of the invention further provides a liquid crystal cell, in which the IR material contained in the IR layer 9 may be doped into the raw material of at least one of the individual components of the liquid crystal cell while fabricating the components, no matter the liquid crystal cell has or has not the IR layer 9. For example, the IR material contained in the IR layer 9 is doped into the raw material of at least one of the following components: the upper polarizer 1, the upper substrate 2, the color filter layer 3, the common electrode 4, the pixel electrode 6, the lower substrate 7, and the lower polarizer 8.

Moreover, the IR material in the IR layer 9 may be surface modified, such that the IR material is compatible and has optimal matching property with the corresponding structure of the liquid crystal cell, so as to prevent the introduction of the IR material from affecting the performance of the LCD. The purpose of the surface modification is to modify the surface morphology, grain boundary structure of the IR material, such that the IR material can be compatible with the corresponding structure of the liquid crystal cell and does not harm the performance of the display device. Meanwhile, a further purpose of the surface modification is to change the activity of the IR material and to improve the heat exchange capacity by modifying the surface morphology, grain boundary structure of the IR material, such that the far-IR light of a specific wavelength is emitted with higher emissivity.

Still another embodiment of the invention provides a surface modification method for an IR material, the method comprises the following steps:

1) nanocrystallizing the IR material to obtain nanoparticles of the IR material; and 2) modifying surface property of the nanocrystallized nanoparticles such that the nanoparticles are compatible and have matching property with a structural layer of a liquid crystal cell and emit IR light when being irradiated.

The purpose of step 1) is to nanocrystallize the IR material to obtain the nanoparticles of the IR material. For fabricating nanomaterial, conventional grinding and dispersion methods may be used, for example, in an organic solvent by using a conventional grinding device (such as a ball mill, a sand mill or the like) and a dispersant. A weight percentage of the IR material in the nano dispersion solution may be 10~15%. As an example, the step 1) comprises grinding and dispersing the IR material to obtain a nano dispersion solution of the IR material with an average particle size of 1 nm to 200 nm.

The purpose of step 2) is to modify the surface property of the nanocrystallized nanoparticles such that the IR material is compatible with the corresponding structure of the liquid crystal cell and does not harm the performance of the display device. Meanwhile, a further purpose of the step 2) is to change the activity of the IR material and to improve the heat exchange capacity by further modifying the surface of the nanocrystallized IR material, such that the far-IR light of a specific wavelength is emitted with higher emissivity. As an example, the step 2) comprises:

mixing the dispersion solution of the IR material with an organic solution containing methyl methacrylate, styrene, maleimide, and then adding an azo-initiator solution into the mixture; and after the reaction is finished, adding a cooling organic solvent to cool and stirring until resultant is cooled, then filtering and drying the resultant to obtain the surface modified IR material.

As another example, the step 2) comprises:

dissolving an azo-initiator, such as 2,2'-Azobis-(2-methylbutyro nitrile), azobis isobutyro nitrile (AIBN), azobis isohexyl nitrile, 2,2'-Azobis isohepto nitrile or the like, in an organic solvent for further use;

placing the nano dispersion solution of the IR material in a 4-mouth flask and performing stirring, vibration (with a frequency of above 50 Hz) or shaking;

dissolving monomer including methyl methacrylate, styrene, and maleimide (the molar ratio of three monomer is 1:1~2:1~2) in an organic solvent (with a volume ratio between the monomer and the organic solvent is 1:1~1:3) and adding the obtained solution into the 4-mouth flask, wherein the IR material weights 8~25%, preferably 10~20%, and more preferably 12~17%, of the total mixture weight;

an environmental condition for modifying the surface property of the nanocrystallized nanoparticles has a temperature of 35° C.~60° C. and in a nitrogen atmosphere; the azo-initiator solution is added drop by drop with a weight of 1~5% of total monomer weight into the 4-mouth flask, a reaction time for stirring, vibration or shaking is 30~90 minutes;

after the reaction is finished, adding a cooling organic solvent of 5° C. to 10° C. to cool and stirring until resultant is cooled to room temperature;

after filtering the resultant for three times, washing the filtered solid using the aforementioned organic solution with dissolved monomer, and then drying at 70° C.~100° C. for 5~20 minutes to obtain the surface modified IR material.

The organic solvent used in the above method may be one or more of fatty alcohol, glycol ethers, ethyl acetate, methyl ethyl ketone (MEK), 4-methylpentan-2-one, monomethyl ether acetate glycol esters, γ-butyrolactone, propionic acid-3-ether acetate, butyl carbitol, butyl carbitol acetate, propylene glycol monomethyl ether, propylene glycol monomethyl ether acetate, cyclohexane, xylene and isopropanol.

The dispersant used in the above method may be a conventional dispersant, such as BYK 410, BYK 110, BYK 163, BYK 161, BYK 2000 or the like. A weight percentage of the dispersant in the nano dispersion solution is 5~15%, preferably 7~12%.

A further embodiment of the invention provides a liquid crystal cell, in which a component comprising an IR material is disposed, the IR material is obtained using the above surface modification method.

A still further embodiment of the invention provides a LCD device comprising a backlight module and any one of the above liquid crystal cell. The LCD device can be a display of a portable electronic device such as a portable PC, a mobile phone, and an E-book.

As the liquid crystal cell in the above embodiments has a component comprising the IR material disposed therein, the liquid crystal cell can emit IR light having relatively strong penetration and radiation capabilities when being irradiated by the backlight module or ambient light (such as solar light) providing irradiation for the liquid crystal cell. When absorbed by the human body, the IR light may cause the in vivo water molecules to resonate, such that the water molecules are activated and the bonding force between the water molecules is increased. As a result, bio-macromolecules such as protein are activated and the bio-cells are in a higher vibrating energy level. As the bio-cells are resonating with each other, the far-IR thermal energy can be transferred to a deeper endermic location of the human body. The temperature at the deeper location therefore increases, and the generated heat is dissipated from inside toward outside, which will expand capillary vessels and facilitate blood circulation, thereby enhancing the metabolism between tissues, increasing regeneration capability of the tissues, and improving immune competence of the body. Such procedure is beneficial for the heath and can reduce the influence of electromagnetic radiation on the human body. Similarly, in the LCD device comprising the liquid crystal cell of the invention, the liquid crystal cell can emit IR light to the exterior of the LCD device when being irradiated by the backlight module or ambient light (such as solar light), which makes the LCD device beneficial for the heath and can reduce the influence of electromagnetic radiation on the human body. Moreover, the surface modified IR material can realize compatibility and optimal performance matching with the liquid crystal cell structure, which will improve the heat exchange capability between the IR material and the backlight as well the ambient light without compromising the performance of the LCD device, and the surface modified IR material will emit far-IR light with higher emissivity.

What are described above is related to the illustrative embodiments of the disclosure only and not limitative to the scope of the disclosure; the scopes of the disclosure are defined by the accompanying claims.

What is claimed is:

1. A liquid crystal cell, wherein a component comprising an infrared (IR) material is disposed in the liquid crystal cell, the liquid crystal cell includes a color filter substrate and an array substrate disposed as opposed to each other, the component comprising the IR material is disposed on the color filter substrate, and the color filter substrate is divided into a pixel region and a black matrix region surrounding the pixel region, the component comprising the IR material is only formed on the black matrix region.

2. The liquid crystal cell according to claim 1, further comprising a upper polarizer disposed at one side of the color filter substrate and a common electrode disposed at the other side of the color filter substrate; the color filter substrate comprises a substrate and a color filter layer, wherein the component comprising the IR material is disposed between the upper polarizer and the substrate.

3. The liquid crystal cell according to claim 1, wherein the IR material is a mixture of one or more of biochar, tourmaline, far-infrared ceramic, jade powder, aluminum oxide, copper (II) oxide, silver(I,III) oxide and silicon carbide.

4. The liquid crystal cell according to claim 1, wherein a particle size of the IR material is in the order of a nanometer to a micrometer.

5. The liquid crystal cell according to claim 1, wherein the IR material is surface modified so as to emit IR light upon being irradiated.

6. A LCD device comprising a backlight module and the liquid crystal cell according to claim 1.

7. A surface modification method for an IR material, comprising:
nanocrystallizing the IR material to obtain nanoparticles of the IR material;
modifying surface property of the nanocrystallized nanoparticles, such that the nanoparticles are compatible and have matching property with a corresponding structural layer of a liquid crystal cell and emit IR light upon being irradiated by light.

8. The method according to claim 7, wherein nano crystallizing the IR material comprises grinding and dispersing the IR material to obtain a dispersion solution of the IR material with an average particle size of 1 nm to 200 nm.

9. The method according to claim 8, wherein modifying surface property of the nanocrystallized nanoparticles comprises:
mixing the dispersion solution of the IR material with an organic solvent containing methyl methacrylate, styrene, maleimide, and then adding an azo-initiator solution into the mixture; and
after the reaction is finished, adding a cooling organic solvent to cool and stirring until a resultant is cooled, then filtering and drying the resultant to obtain the surface modified IR material.

10. The method according to claim 9, wherein a molar ratio between methyl methacrylate, styrene and maleimide is 1:1~2:1~2, the IR material weights 8~25% of the total mixture weight; and the azo-initiator solution is added drop by drop with a weight of 1~5% of total monomer weight.

11. The method according to claim 9, wherein an environmental condition for modifying the surface property of the nanocrystallized nanoparticles has a temperature of 35° C.~60° C. and in a nitrogen atmosphere;
a reaction time is 30 minutes to 90 minutes;
a temperature of the cooling organic solvent is 5° C. to 10° C.;
cooling is performed till room temperature;
filtering is performed for three times; and
drying is performed for 5 minutes to 20 minutes at 70° C. to 100° C.

* * * * *